United States Patent [19]

Von Criegern et al.

[11] Patent Number: 4,860,225
[45] Date of Patent: Aug. 22, 1989

[54] METHOD AND APPARATUS FOR STORING MEASURED DATA FROM SUB-REGIONS OF A SPUTTER CRATER WHICH IS GENERATED AND ANALYZED IN A SECONDARY ION MASS SPECTROMETER

[75] Inventors: Rolf Von Criegern, Geretsried; Peter Fazekas, Munich; Johannes Fottner, Jetzendorf, all of Fed. Rep. of Germany

[73] Assignee: Siemens Aktiengesellschaft, Berlin and Munich, Fed. Rep. of Germany

[21] Appl. No.: 183,336

[22] Filed: Apr. 7, 1988

Related U.S. Application Data

[63] Continuation of Ser. No. 56,276, May 26, 1987, abandoned.

[30] Foreign Application Priority Data

Sep. 30, 1983 [DE] Fed. Rep. of Germany ....... 3335625

[51] Int. Cl.$^4$ .......................... G21K 5/04; G06F 15/36
[52] U.S. Cl. ............................ 364/551.01; 250/492.2; 250/492.3
[58] Field of Search ........................... 364/555, 551.01; 250/309, 310, 492.2, 492.3; 382/67

[56] References Cited

U.S. PATENT DOCUMENTS

| | | | |
|---|---|---|---|
| 3,686,499 | 8/1972 | Omura et al. | 250/309 |
| 3,694,635 | 9/1972 | Hoetzel et al. | 250/310 X |
| 3,881,108 | 4/1975 | Kondo et al. | 250/307 |
| 3,889,115 | 6/1975 | Tamura et al. | 250/309 X |
| 3,916,191 | 10/1975 | Leys et al. | 250/309 X |
| 4,132,898 | 1/1979 | Buelow et al. | 250/492.2 |
| 4,147,928 | 4/1979 | Crean et al. | 382/67 X |
| 4,164,652 | 8/1979 | Wollnik | 250/282 X |
| 4,363,953 | 12/1982 | Katsuta et al. | 250/492.2 X |
| 4,491,926 | 1/1985 | Okada et al. | 364/555 |
| 4,514,822 | 4/1985 | Schneider et al. | 364/498 |
| 4,540,884 | 9/1985 | Stafford et al. | 250/282 |

FOREIGN PATENT DOCUMENTS

2023688 11/1970 Fed. Rep. of Germany .

OTHER PUBLICATIONS

Jupijn et al.: Description of the Use of an EPROM for the Automatic Base Line Control of a Single-Beam Spectrophotometer. The Institute of Physics 1979, J. Scientific Instruments vol. 12, pp. 294-297.
Takagi et al.: High Speed Image Process for Picosecond Time-Resolved Spectrography, Rev. Scientific Instruments vol. 52, No. 7, Jul. 1981, pp. 1003-1009.
Rüdenauer F. G. et al., "A Further Step Towards Three-Dimensional Elemental Analysis of Solids", (see sheet 2).
Liebl H., "Ion Probe Microanalysis", Journal of Physics E; Scientific Instruments, vol. 8, No. 10, 1975, pp. 797-808.
Huber A. M. et al., "Quantitative Analysis of Oxygen in Thin Epitaxial Layers of GaAs By SIMS" (see sheet 2). Mikrochimica Acta, (Wien), 1981, II, pp.375-389.
Nuclear Instruments and Methods, vol. 149, 1978, pp. 543-546.
Degréve F., "Depth Profiling by Ion Microprobe with High Mass Resolution", International Journal of Mass Spectrometry and Ion Physics, vol. 29, 1979, pp. 351-361.

*Primary Examiner*—Felix D. Gruber
*Attorney, Agent, or Firm*—Hill, Van Santen, Steadman & Simpson

[57] ABSTRACT

A method and an apparatus for storing measured data from a sputter crater which is generated and analyzed in a secondary ion mass spectrometer is considerably more simple and cost-effective than techniques requiring complete data storage and is an improvement over the known standard integral method. The region swept by the ion beam of a secondary ion mass spectrometer is subdivided into a plurality of sub-areas, one location in a memory is assigned to each of the sub-areas, the signal components occurring from the individual sub-areas are stored in the assigned memory locations during a sweep of the sputter crater with the ion beam, and the measured data are evaluated after the end of at least one scan of the sputter crater.

19 Claims, 2 Drawing Sheets

METHOD AND APPARATUS FOR STORING MEASURED DATA FROM SUB-REGIONS OF A SPUTTER CRATER WHICH IS GENERATED AND ANALYZED IN A SECONDARY ION MASS SPECTROMETER

This is a continuation of application Ser. No. 056,276, filed May 26, 1987 now abandoned.

BACKGROUND OF THE INVENTION

1. Field of the Invention

The invention relates to a method and to an apparatus for the storage of measured data from a sputter crater which is generated and analyzed in a secondary ion mass spectrometer.

2. Description of the Prior Art

Given the analysis technique of secondary ion mass spectrometry (SIMS), an ion beam is scanned line-by-line across a specimen in a known manner and a sputter crater is thereby created in the specimen. The ion-like erosion products (secondary ions) thereby occurring are supplied to a mass spectrometer and analyzed. Given a registration of the signal intensity of the secondary ions of a specific type of ion as a function of time, a so-called depth profile for the appertaining chemical element with respect to the specimen under investigation is thereby obtained. Given an integral measurement, the secondary ions from the entire region of the sputter crater thereby contribute to the signal intensity of the secondary ions. In general, however, the measurement is restricted to the central region of the sputter crater with the assistance of an electronic gate circuit ("gate") in order to blank effects of the crater rim. Should inhomogeneities of the specimen occur within the crater region during the course of an analysis, then it is not possible, given the integral method, to undertake a discrimination of secondary ion signal contributions from different sub-regions and to eliminate the inhomogeneities.

It is known from a publication of F. G. Rüdenauer et al, in Mikrochimica Akta (Vienna), 1981 II, pp. 375-389 that the ion beam in a secondary ion mass spectrometer to be swept across a specimen point-by-point from one point to a next point in small individual or discrete steps with the assistance of a computer, that the secondary ion signal contributions from each one of these individual points can be stored, and that evaluations can be executed in this manner wherein the assignment of the measured values to that location on the specimen from which they derive is maintained. This known method, however, requires a considerable expense since a process computer having an extensive mass storage on the order of 100 MBytes is required for this purpose.

Furthermore, an interface unit for controlling the ion beam by the computer must be produced for the implementation of this method.

SUMMARY OF THE INVENTION

The object of the present invention is to provide a method and an apparatus of the type generally set forth above which is considerably more simple and more cost-effective than a method and an apparatus for complete data storage which nonetheless exhibit a significant progress over the integral The above object is achieved, according to the present invention, in a method in which at least one part of the region swept by the ion beam of the secondary ion mass spectrometer is divided into a plurality of subareas, in that one location in a memory is assigned to each of these subareas, in that during scanning of the sputter crater with the ion beam, the signal components occurring from the individual subareas are deposited in the memory at the location assigned to the respective subarea, and in that the measured data are evaluated at the end of at least one scanning of the sputter crater.

According to the invention, a counter is provided for counting the secondary ion signals, a temporary memory is provided for temporary storage of the counter contents that occur in the counter unit during the sweep of the sputter crater, and a central control is provided for controlling the counter unit and the temporary memory as a function of the position of the ion beam.

Accordingly, a region of a specimen swept by an ion beam of a secondary ion mass spectrometer is, according to the invention, subdivided into a number of sub-areas as, for example, a chessboard. One location in a temporary memory is assigned to each sub-area of the region of the specimen swept by the ion beam. Then, while the ion beam sweeps the entire region of the sputter crater once, the secondary ion signal components coming from the individual sub-areas of the overall region are deposited in an ordered manner in the temporary memory and are communicated to a computer at the end of the sweep. The set of measured data of such a scanning pass represents an element distribution image for chemical elements that are present in the specimen. A sequence of such sets of measured data or element distribution images arises as a result of a sequence of sweeps. After the end of a measurement, the stored measured data can be evaluated in a number of different ways.

BRIEF DESCRIPTION OF THE DRAWINGS

Other objects, features and advantages of the invention, its organization, construction and operation will be best understood from the following detailed description, taken in conjunction with the accompanying drawings, on which.

DESCRIPTION OF THE PREFERRED EMBODIMENTS

Given the analysis technique of secondary ion mass spectrometry (SIMS), a specimen to be analyzed with respect to its elemental composition is bombarded with an ion beam (for example, oxygen $O_2^+$, at 1-15 keV, and 1 nA-10 μA) and is thereby slowly eroded in a sputtering process. The atoms and molecule fragments thereby released (sputtered off) from the specimen surface can, insofar as they are electrically charged ("secondary ions"), be steered into a mass spectrometer, be separated in the mass spectrometer according to their mass/charge ratio m/e, and be detected and counted with the assistance of a multiplier or the like.

In order to achieve a uniform erosion of the specimen over the area to be analyzed, the ion beam is usually focused on the surface of the specimen and swept line-by-line across the area of the specimen which is to be eroded. An apparatus, such as an a-DIDA machine produced by Atomika GmbH, Munich, Federal Republic of Germany, can be employed as the scanning ion beam device.

FIGS. 1A–1D illustrate a few possibilities for the evaluation of measured data that have been acquired with the method of the invention. If at least one inner region (image area BF) of a sputter crater SK has been subdivided in the manner of a chessboard into $8 \times 8 = 64$ fields which function as sub-areas, in an integral form of measured data as shown, for example, in the example of FIG. 1A can be achieved by the respective summation of the data appertaining to a single sweep and deriving from, for example, the 64 sub-areas of the image area BF.

Figure 1A:
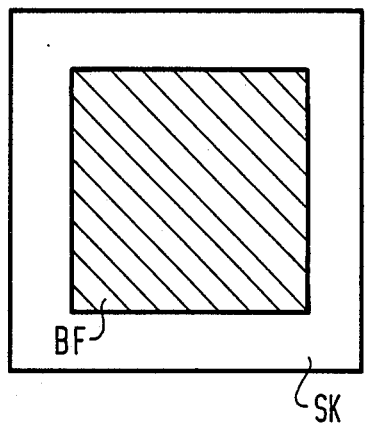
FIGS. 1a-1d illustrate various possibilities for the measured data evaluation in accordance with the method of the invention.
Figure 1B:
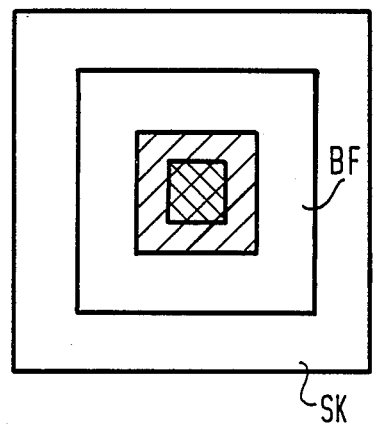

Referring to the example in FIG. 1B, sub-areas of the sputter crater SK can be combined into concentric regions of different sizes, so that integral measured values obtained by using different blanking of the crater rim can be achieved in this manner. When the respective measured data from all sub-areas lying within a concentric region are summed, then the different results thereby achieved correspond to those results that would be achieved given different types of integral measurements if variable electronic "gate" regions were to provide blanking of the crater rim to respectively degrees in the different integral measurements. The invention enables only a single measurement to be executed and that an optimum blanking of the crater edge be determined only after the end of the single measuring pass. An optimum blanking of the crater rim is defined in that, on the one hand, there is possibly no influence of the crater rim in the measured data and that, on the other hand, the greatest possible area of the sputter crater contributes to the final result. According to the known art, an optimum blanking of the crater rim could only be specified after a number of repeated measurements have been executed with different blankings of the crater rim.

Figure 1C:
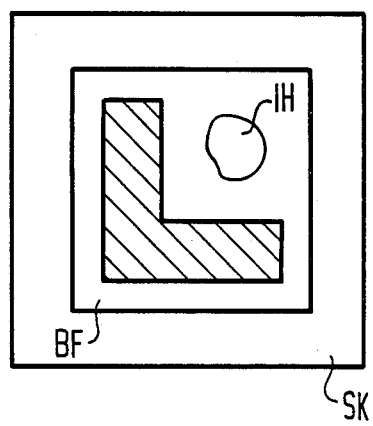

Referring to FIG. 1C, an inhomogeneity IH occurs inside the sputter crater SK. The appearance of an inhomogeneity IH within the sputter crater SK can therefore be immediately identified by comparison of the measured data which are acquired from the various sub-areas of the image area BF. When an inhomogeneity IH appears within the sputter crater SK during the course of a depth profile measurement, then the measured data from respectively identical sub-areas, such as shown with shading in FIG. 1C, can be combined and depth profiles of the various zones of the sputter crater SK can be acquired in this manner.

Figure 1D:
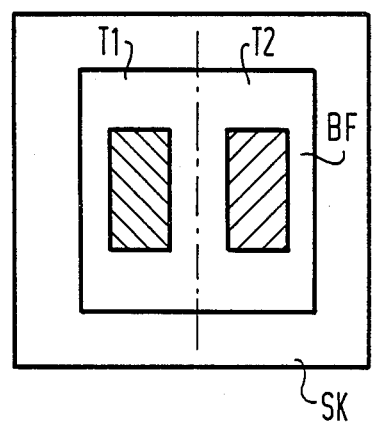

Referring to FIG. 1D, a special case of the example of FIG. 1C is illustrated. A specimen, for example a semiconductor wafer, has been intentionally differently pretreated in two mutually adjacent sub-regions T1 and T2. A respective depth profile measurement on each sub-region T1 and T2 is to be prepared in order to reveal the differences in the various sub-regions T1 and T2 by comparison, the differences being rather slight under given conditions.

Whereas a respective depth profile measurement in two mutually adjacent sub-regions T1 and T2 was previously possible only by way of two different measuring passes, measuring in accordance with the present invention can be carried out across the boundary line between the two subregions T1 and T2, whereby this boundary line should also be a boundary line between different sub-areas of the sputter crater SK insofar as possible. After conclusion of the measurement, the measured data from the two different regions T1 and T2 can be separately represented, given the method of the present invention. A differential measurement of the different depth profiles in the sub-regions T1 and T2 executed in this manner with the method of the present invention contains fewer mensurational tolerances than do two independent, successively executed depth profile measurements according to the prior art.

Such sub-areas whose measured data are summed are respectively illustrated in shaded form in the same manner in FIGS. 1A–1D.

Figure 2:
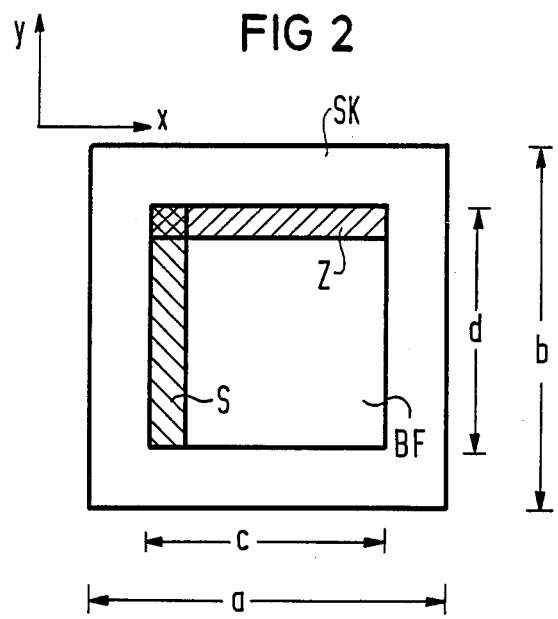
FIG. 2 is a graphic illustration of the sub-division of a sputter crater into sub-areas according to the invention.

FIG. 2 illustrates the division of a sputter crater SK into sub-areas according to the invention. The area of the sputter crater SK is referred to as the crater area and has a width a and a length b. The crater area is the area swept on the specimen by the ion beam in a scanning pass. That portion of the crater area from which measured data are registered and stored is referred to as the image area BF and has a width a and a length d in FIG. 2. Given the secondary ion mass spectrometer mentioned above of the Atomika company, the ion beam is guided across the crater area in 256 lines with the assistance of a sweep generator. A line is thereby a linear trace of the ion beam on the specimen given passage in the x direction and given a constant y coordinate. The image area can be sub-divided into a number of line strips Z. Each line strip Z thereby has the width c and a length which amounts to a fraction of the length d of the image area. On the other hand, the image area can also be subdivided into column strips S. The column strips have the same length d as the image area and their widths amount to a fraction of the width c of the image area. In the exemplary embodiment described below, the image area shall be sub-divided into n column strips S and m line strips Z. When the image area is selected smaller than the crater area, storage capacity can be saved by omitting an edge region of the crater area when storing the measured data.

Figure 3:
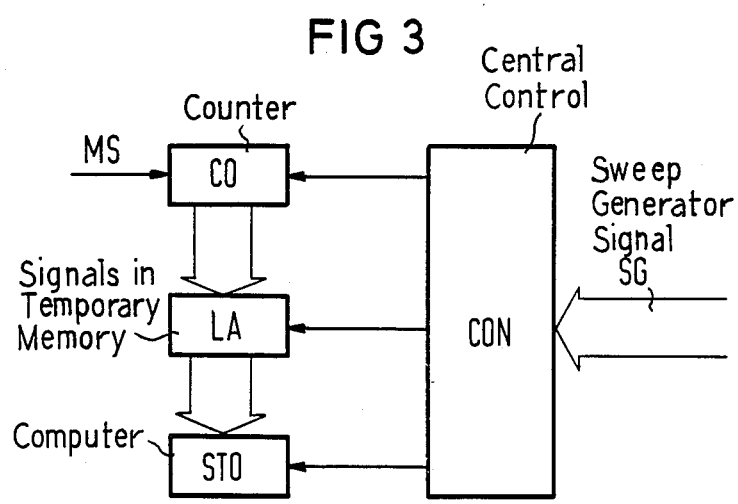
FIG. 3 is a schematic representation of apparatus for carrying out the method of the invention.

FIG. 3 illustrates an apparatus for storing measured data from sub-areas of a sputter crater SK. When the method of the invention is based, for example, on an image area having eight line strips Z and eight column strips S, i.e. having $8 \times 8$ image segments, then the measuring sequence can be described as follows. A counter unit CO comprises eight counters which are permanently assigned to the eight column strips S on the image area. The counter unit CO is a unit constructed of eight digital counters. The eight column strips of the image area are traversed in every line pass of the ion beam of the specimen and each of the eight counters of the counter unit CO is addressed when the respectively assigned column strip is traversed. The switch from one counter to another counter in the counter unit CO occurs by way of comparison of the column numbers of the sweep generator with those column numbers which had been fixed before execution of the test as boundary column numbers between respectively two mutually adjacent column strips S in accordance with a desired division of the image area into column strips S. Such a comparison of the current column numbers with the preselected boundary column numbers at the boundaries between mutually adjacent column strips S can occur, for example, by comparators.

Every image segment is exactly assigned to one line strip Z and one column strip S. All sub-results from one and the same image segment are summed in that counter of a counter unit CO assigned to the column strip S of the image segment when sweeping a line strip Z until the ion beam traverses the width of the corresponding line strip Z for the last time. During this last line traversal within the line strip Z, the respective summed counter contents which are contained in the specific column counter are transferred into a temporary memory LA as soon as the ion beam departs the respective image segment within the line strip Z, and the corresponding counter content which reproduces the measured data from this image segment is erased in the counter unit CO. This sequence of the measurement is repeated for each of the following line strips Z.

When the entire image area has been swept by the ion beam, therefore, the 64 counter results from the 64 image segments of the image area subdivided into eight column strips S and eight line strips Z are ready in the temporary memory LA for transfer into a computer STO.

The signal components are stored in the respective assigned locations for each scan of the sputter crater and the signals are processed with a computer at the end of each scan of the sputter crater The measured data is stored as a function of the individual sub-areas and the individual scans of the ion beam and the measured data of a scan is summed. The measured data from identical sub-areas is summed to obtain a depth profile of an inhomogeneity of the sputter crater and the measured data from two sub-regions are separately evaluated to obtain their depth profiles and the differences between them.

Accordingly, only eight counters are required in practicing the present invention for the acquisition of the 64 measured quantities from the 64 image segments.

A central control CON is required in order to control the counter unit CO and the temporary memory LA as a function of the position of the ion beam. The central control CON receives a signal SG from the sweep generator, the signal SG containing the column number and the line number of the respective position of the ion beam on the sputter crater SK. As a function of this signal SG, the counter unit CO receives a signal from the central control CON with respect to which counter should acquire the respective signal MS from the mass spectrometer. Upon conclusion of scanning of the respective image element, the central control initiates the transfer of the corresponding counter content from the counter unit CO to the corresponding storage location in the temporary memory LA, then initiates the cancellation of this counter content which was transferred into the temporary memory LA in the counter unit CO, and, finally, controls the transfer of the counter results contained in the temporary memory LA into the computer STO.

The line strips Z and column strips S need not have a uniform and shared width or, respectively, length.

The image area need not be equal in coverage to the crater area. A frame comprising a few lines and columns can be provided at the edge of the crater area in order to reduce the influences of the crater rim, the specimen in fact being sputtered in the frame region but not providing the signals MS to be recorded therefrom in order to maintain the memory requirements low.

Although we have described our invention by reference to particular illustrative embodiments thereof, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

We claim:

1. In a method for storing test data and which substantially reduces the required memory capacity in which an ion beam is focused on a specimen and is deflected for scanning line-by-line over a plurality of sub-regions of the specimen surface, in which secondary particles are triggered on the specimen by a sputtering process in response to the ion beam for detection and processing, the improvement therein comprising the steps of: subdividing at least one part of the surface scanned by the ion beam into a plurality of sub-areas defined by scanning lines and columns; registering in a plurality of counters test data which indicates the number of secondary particles released during the scanning of each line of the individual sub-areas and wherein each counter registers test data for one column and wherein each counter corresponds to a different column, transferring after each line scan the stored data from said plurality of counters to a temporary memory, and a region of said temporary memory assigned to the respective sub-area, erasing the data in said plurality of counters, and transferring the test data in said temporary memory to a computer and evaluating the test data after at least one line scan of the sputter crater generated by the ion beam.

2. The method of claim 1, and further comprising the step of:
combining the stored test data of the individual memory areas after scanning.

3. The improved method of claim 1, and further comprising the step of:
combining the test data from memory areas whose assigned sub-areas form concentric areas of different size within the sputter crater.

4. The method of claim 1, and further comprising the steps of:
identifying an inhomogeneity occurring within the sputter crater by comparing the test data stored in the various memory areas; and
combining the test data of the individual sub-areas outside of the inhomogeneity for producing a depth profile.

5. The improved method of claim 4, and further comprising the steps of:
for two service regions of a specimen adjacent to one another which are differently pre-treated and scanned with the ion beam, storing the test data in memory areas assigned to the respective regions;
independently evaluating the test data in the memory areas for producing a depth profile; and
identifying the differences of the surface regions by comparing the identified depth profiles.

6. The method of claim 1, and further comprising the steps of:
identifying an inhomogeneity occurring within the sputter crater by comparing the test data stored in the various memory areas; and
combining the test data of the individual areas in the region of the inhomogeneity to produce a depth profile.

7. The improved method of claim 6, and further comprising the steps of:
for two service regions of a specimen adjacent to one another which are differently pre-treated and scanned with the ion beam, storing the test data in memory areas assigned to the respective regions; independently evaluating the test data in the memory areas for producing a depth profile; and identifying the differences of the surface regions by comparing the identified depth profiles.

8. Apparatus for storing measured data from a sputter crater generated and analyzed in a secondary ion mass spectrometer which scans line-by-line the crater with an ion beam which substantially reduces the required memory capacity comprising: a counting unit including a plurality of counters for receiving and counting secondary ion signals from a plurality of sub-areas of a region of each scan line and each of said plurality of counters receiving the signals for a different column, temporary memory means connected to said plurality of counters of said counting unit and temporarily storing the contents of said plurality of counters of each counting unit for each line sweep of the ion beam over the respective sub-areas; a control unit connected to said plurality of counters for switching said counters and for controlling the storage into said temporary memory means as a function of the position of the ion beam; and computer means connected to said control unit and connected to said temporary memory means for evaluating the contents of said memory means after at least one line scan of the sputter crater generated by the ion beam.

9. A method for storing and evaluating measured data from a sputter crater generated in a secondary ion mass spectrometer which substantially reduces the required memory capacity, whereby an ion base is deflected on a specimen and whereby the secondary ions triggered on the specimen are documented, comprising the steps of:
(a) subdividing at least one sub-region of the specimen into a plurality of non-overlapping sub-surfaces;
(b) assigning each of the sub-surfaces respectively a memory location in a first memory unit;
(c) deflecting the ion beam over a sub-area of the specimen;
(d) respectively detecting the measured data from the same sub-surface and registering it in a counter allocated to the sub-surface and said data are summed up; and
(e) storing after the scanning of a sub-surface, a measured value representing the sum of the respective measured data in a memory location of a second memory allocated to the sub-surface.

10. A method according to claim 9, comprising scanning a first group of sub-surfaces and, subsequently, at least one second group of sub-surfaces with the ion beam; and executing again the method steps (d) and (e) of claim 1 are respectively executed during the scanning of the first and of the second group of sub-surfaces.

11. A method according to claim 9 or 10, wherein the sub-region is subdivided a first direction into a first plurality of strip-shaped line regions; and the sub-region is subdivided in a second direction into a second plurality of strip-shaped column regions; and the common area of said second strip-shaped regions respectively defines a sub-surface.

12. A method according to claim 11, wherein the first and the second direction make an angle of 90°.

13. A method according to claim 9 or 10, wherein the measured values are read into a second memory unit after the scanning of the sub-region.

14. A method according to claims 9 or 10, wherein the sub-region is multiply scanned; and storing the measured values as a function of the individual scans.

15. A method according to claims 9 or 10, wherein the measured values are summed up.

16. A method according to claims 9 or 10, wherein the measured values of the sub-surfaces covering a concentric region of the specimen are summed up.

17. A method according to claims 9 or 10, wherein the measured values of the sub-surfaces comprising an inhomogeneity are summed up.

18. A method according to claims 9 or 10, wherein the measured values of the sub-surfaces that comprise no inhomogeneity are summed up.

19. A method according to claims 9 or 10 wherein the specimen is differently pre-treated in a first and in a second region; and the measured values from the regions adjoining one another are separately evaluated in order to obtain the respective depth profiles.

* * * * *